US00PP34711P2

(12) United States Plant Patent
Rimland

(10) Patent No.: US PP34,711 P2
(45) Date of Patent: Nov. 1, 2022

(54) ***DIEFFENBACHIA SEGUINE* PLANT NAMED 'A1'**

(50) Latin Name: *Dieffenbachia seguine*
Varietal Denomination: A1

(71) Applicant: Michael K. Rimland, Miami, FL (US)

(72) Inventor: Michael K. Rimland, Miami, FL (US)

(73) Assignee: Costa Farms, LLC, Miami, FL (US)

( * ) Notice: Subject to any disclaimer, the term of this patent is extended or adjusted under 35 U.S.C. 154(b) by 0 days.

(21) Appl. No.: 17/803,147

(22) Filed: Mar. 7, 2022

(51) Int. Cl.
*A01H 5/12* (2018.01)
*A01H 6/10* (2018.01)

(52) U.S. Cl.
USPC ..... Plt./378

(58) Field of Classification Search
USPC ..... Plt./378
CPC ... A01H 5/12; A01H 5/00; A01H 6/10; A01H 6/00; A01H 6/12
See application file for complete search history.

(56) References Cited

U.S. PATENT DOCUMENTS

PP7,298 P * 8/1990 Vanderlaan ..... Plt./378
PP9,694 P * 11/1996 Henny ..... Plt./378

* cited by examiner

*Primary Examiner* — June Hwu
(74) *Attorney, Agent, or Firm* — Adrienne Love

(57) ABSTRACT

A new and distinct *Dieffenbachia seguine* cultivar named 'A1' is disclosed, characterized by mottled variegated leaves in light green which fades to light grey along midrib, mottled light grey patches and dark green secondary venation, dark green margins and moderate light green primary vein. The new variety is a *Dieffenbachia seguine*, normally produced as an ornamental plant.

4 Drawing Sheets

Latin name of the genus and species of the plant claimed: *Dieffenbachia seguine.*

Varietal denomination: 'A1'.

CROSS-REFERENCES TO RELATED APPLICATIONS

None.

STATEMENT REGARDING FEDERALLY SPONSORED RESEARCH OR DEVELOPMENT

None.

BACKGROUND OF THE INVENTION

The present invention relates to a new and distinct cultivar of *Dieffenbachia*, botanically known as *Dieffenbachia seguine*, and hereinafter referred to by the name 'A1'.

The new *Dieffenbachia* plant cultivar was discovered and selected by Michael K. Rimland from a naturally occurring, single plant mutation of *Dieffenbachia* within a population of *Dieffenbachia* plants in a shadehouse in a controlled plant nursery in Miami, Fla., U.S. Asexual reproduction of the 'A1' by tissue culture cuttings was first performed in September 2018 in Miami, Fla. U.S. and has shown that the unique features of this cultivar are stable and reproduced to true to type in successive generations of asexual reproduction.

SUMMARY OF THE INVENTION

The cultivar 'A1' has not been observed under all possible environmental conditions. The phenotype may vary somewhat with variations in environment such as temperature, day length, and light intensity without, however, any variance in genotype.

The following traits have been repeatedly observed and are determined to be the unique characteristics of 'A1'. These characteristics in combination distinguish 'A1' as a new and distinct *Dieffenbachia seguine* cultivar:

1. Exhibits light green leaves with dark green leaf veins, pinnately arranged.
2. Exhibits mottled variegation in light grey.
3. Exhibits dark green thin margins on leaves.

Plants of 'A1' can be compared to plants of the species selection, *Dieffenbachia seguine*. However, 'A1' differs from the plants of the mutation species selection in the following characteristics:

1. Plants of 'A1' produced variegated leaves that have three colors, where the veins and margin are dark green, the light green color on leaves between veins fading to light grey color along midribs and the light grey color mottled on the leaves.

Plants of the new *Dieffenbachia* can be compared to plants of the *Dieffenbachi memoria* 'TIKI,' disclosed in U.S. Plant Pat. No. 7,298. In a side-by-side comparison, however the new *Dieffenbachia* named 'A1' differs from plants of 'TIKI' in the following characteristics:

1. Plants of 'A1' have leaves that are significantly less mottled than the leaves of *Dieffenbachia memoria* Tiki.
2. The leaves of 'A1' are less wavy than the leaves of Tiki.
3. The base leaf color of 'A1' (light green 144D) is much lighter than the base leaf color of Tiki (dark green 139A).

BRIEF DESCRIPTION OF THE PHOTOGRAPHS

The colored photographs herein illustrate the overall appearance of the new *Dieffenbachia* showing the colors as true as it is reasonably possible to obtain in color reproductions of this type. Colors in the photograph may differ slightly from the color values cited in the detailed botanical description of the new variety which accurately describes the colors of the new *Dieffenbachia* plant.

DETAILED BOTANICAL DESCRIPTION OF THE NEW VARIETY

Figure 1:
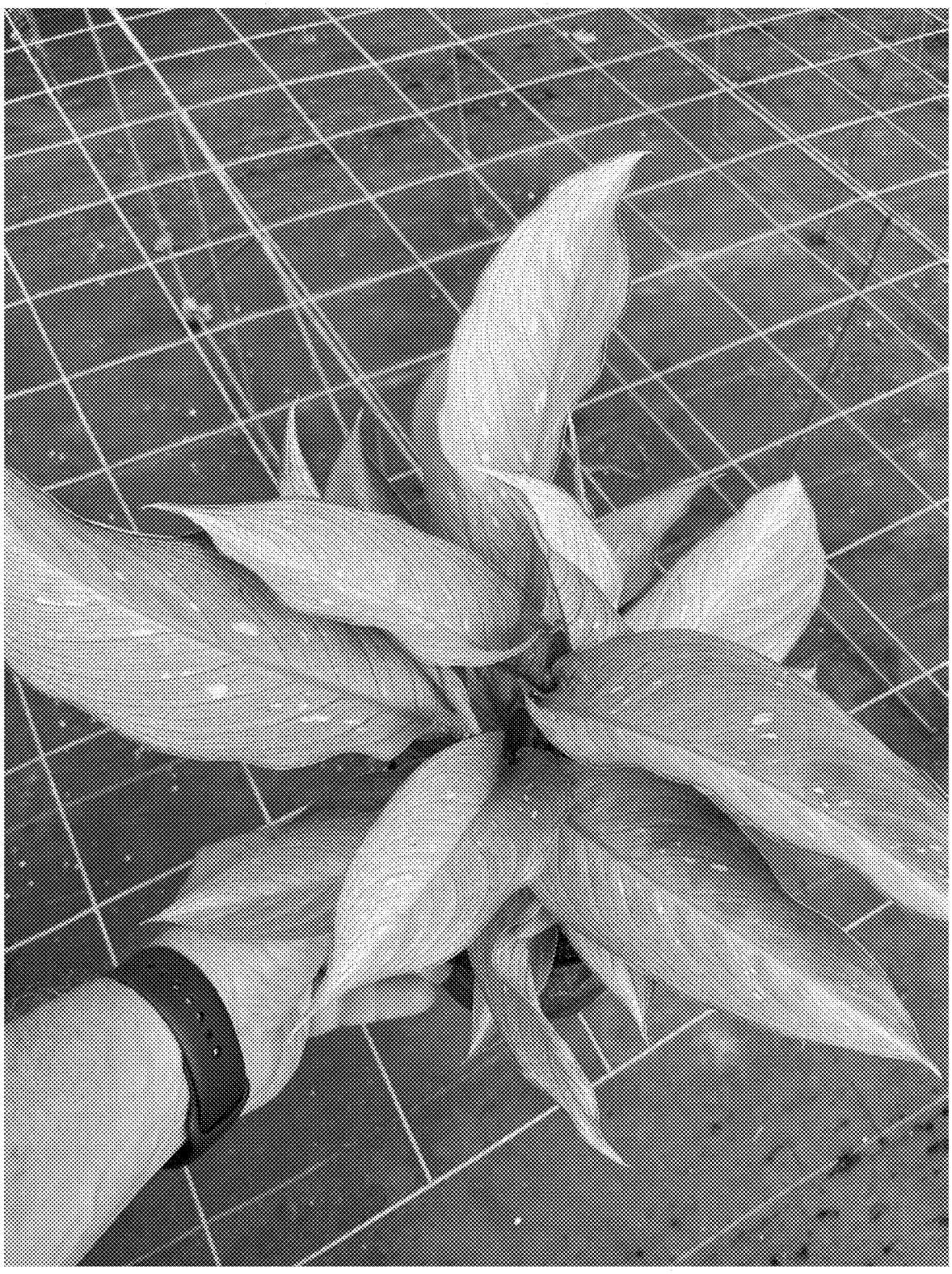
FIG. 1 is a perspective top view of a typical plant of 'A1', grown in a 9 cm diameter container.
Figure 2:
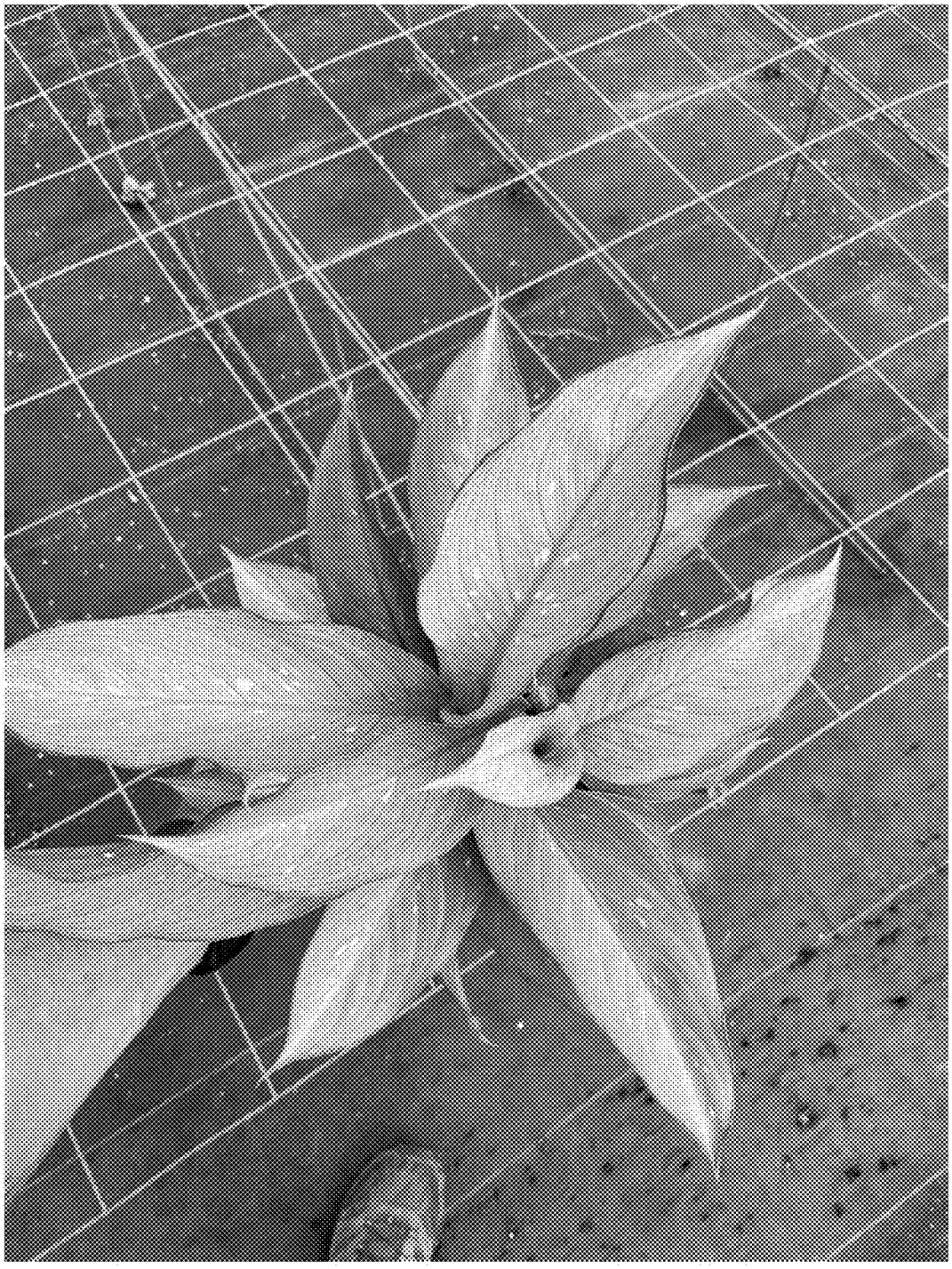
FIG. 2 is a perspective top view of a typical plant of 'A1', grown in a 9 cm diameter container.
Figure 3:
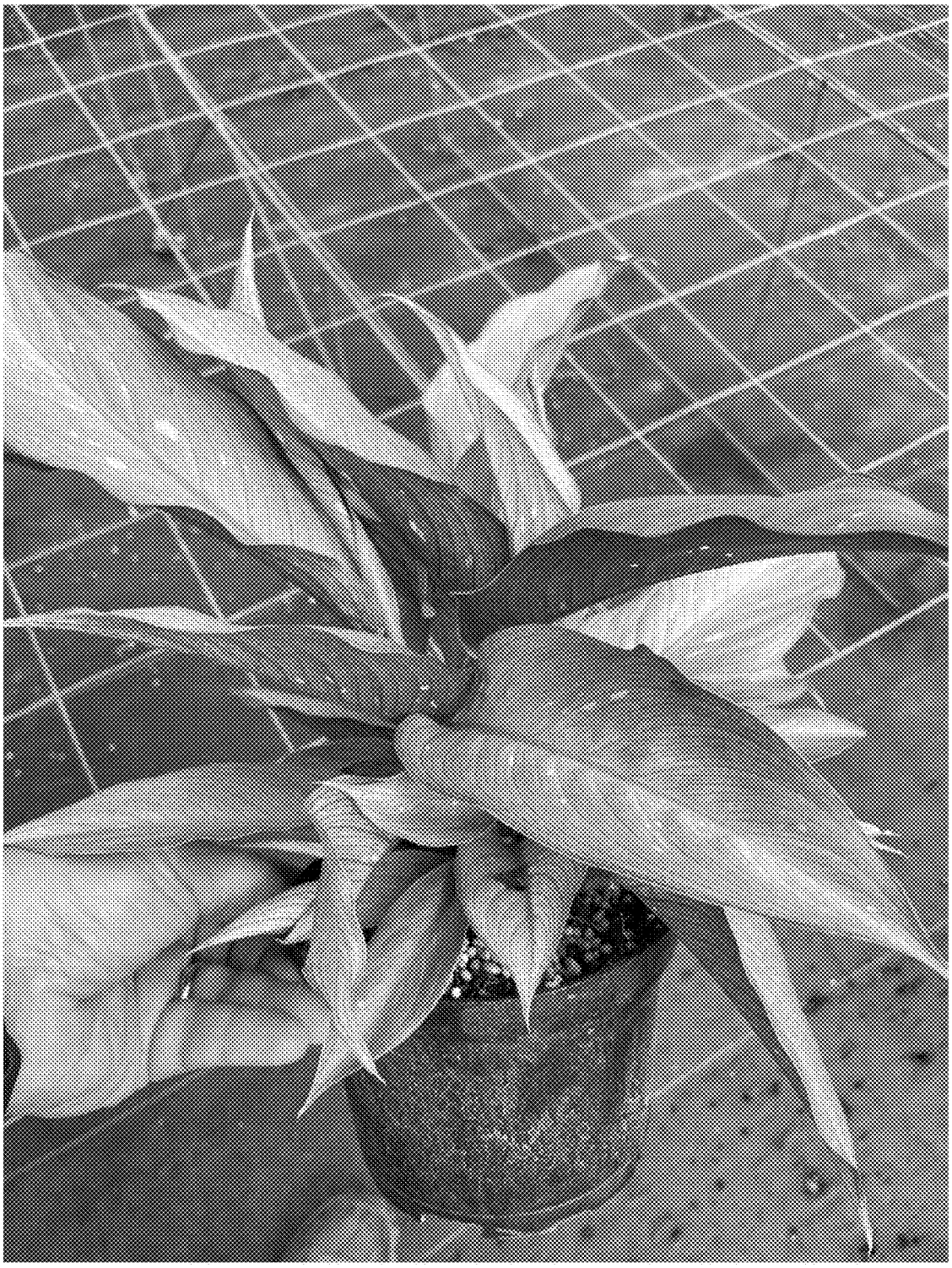
FIG. 3 is a perspective view of a typical plant of 'A1', grown in a 9 cm diameter container.
Figure 4:
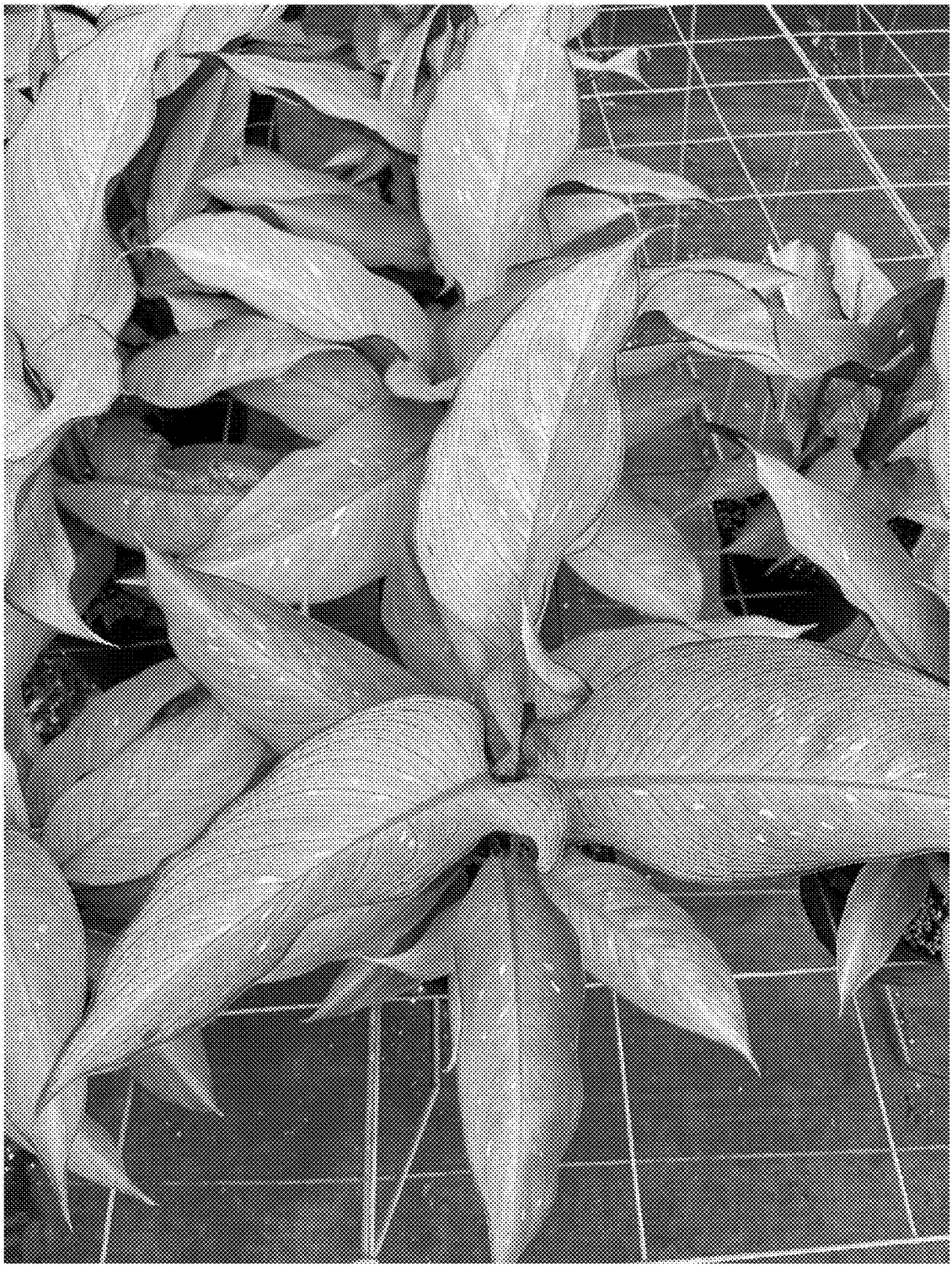
FIG. 4 is a perspective view of a typical foliar variegation of 'A1', illustrating the variegation of many leaves.

The aforementioned photographs and the following observations, measurements, and values describe plants of the new *Dieffenbachia* grown in Miami, Fla. (U.S.) in conditions of 80% shading and 24 hr ventilation all year around in 9 cm containers and under cultural practices of commercial *Dieffenbachia* production. During the production of the plants, temperatures ranged from about 60 (winter)-100 (highest in summer) degrees Fahrenheit and light levels were normal sunlight. Plants were growing about 16 weeks when the photographs and the description were taken.

The following is a detailed description of the new plant characteristics with color in terminology in accordance with The Royal Horticultural Society Colour Chart, Edition V (2007), except where ordinary dictionary significance of color is indicated.

Botanical classification: *Dieffenbachia seguine*.

Common name: 'A1'.

PROPAGATION

Type: By cuttings.

Time to initiate roots, summer: About 14 days.

Time to initiate roots, winter: About 21 days.

Time to produce a rooted young plant, spring: About 45 days.

Root description: Thick and dense.

PLANT

Growth habit: Upright.

Plant shape: Plants are full.

Height (from soil level to top of leaf plane): Approximately 30-40 cm to top of highest leaf.

Plant diameter or spread: Approximately 15 inches.

Growth rate: Fast.

Age of plant described: Approximately 16 weeks.

FOLIAGE

Leaves:

*Arrangement*.—Alternate.

*Average length*.—About 7-8 inches.

*Average width*.—About 3 inches.

*Shape of blade*.—Ovate.

*Apex*.—Acuminate, pointy.

*Base*.—Rounded to slightly cordate.

*Margin*.—Entire, slightly wavy.

*Texture of top and bottom surface*.—Top, smooth; bottom, slightly smooth and slightly rugose with furrowed venation.

*Leaf internode length*.—Approximately 12 mm.

*Color*.—Mature leaves, upper surface: Base color of light green 144D, with light grey 192D highlights close to the midrib of leaves with mottled light grey 192D patches on upper surface; Venation, dark green 141B along secondary veins and margin and moderate light green 145A along midrib; Mature leaves, lower surface: primary color light green 144D, with venation in dark green 141B along secondary veins and margin.

*Venation*.—Reticulate.

*Glossiness*.—Slight gloss.

*Flexibility*.—Medium flexibility.

Petiole:

*Length*.—50 mm.

*Diameter*.—About 2 to 3 mm.

*Strength*.—Strong.

*Texture*.—Smooth.

*Color*.—Light green 144D.

Stem:

*Diameter*.—Average.

*Color*.—Moderate light green 145A.

FLOWER

Blooming not observed on the new cultivar.

OTHER CHARACTERISTICS

Seed production: No seed production to date has been observed.

Temperature tolerance: Normal tropical conditions.

Other distinctive characteristics: Overall commercially interesting appearance. 'A1' has a unique coloring on its leaves. 'A1' has a primary color of light green 144D which fades to light grey 192D near midrib of leaves, with visible venation in dark green 141B and along margins of leaves. 'A1' includes light grey 192D mottled patches on leaves.

What is claimed is:

1. A new and distinct cultivar of *Dieffenbachia seguine* plant named 'A1' as illustrated and described.

* * * * *